United States Patent
Hamaguchi et al.

(10) Patent No.: US 9,259,169 B2
(45) Date of Patent: Feb. 16, 2016

(54) VISCERAL FAT MEASUREMENT DEVICE

(75) Inventors: Takehiro Hamaguchi, Kyoto (JP); Shojiro Oku, Kyoto (JP); Yoshitake Oshima, Kyoto (JP); Toshikazu Shiga, Otsu (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 678 days.

(21) Appl. No.: 12/449,150

(22) PCT Filed: Mar. 17, 2008

(86) PCT No.: PCT/JP2008/054896
§ 371 (c)(1),
(2), (4) Date: Aug. 7, 2009

(87) PCT Pub. No.: WO2008/123044
PCT Pub. Date: Oct. 16, 2008

(65) Prior Publication Data
US 2010/0081962 A1    Apr. 1, 2010

(30) Foreign Application Priority Data
Mar. 19, 2007    (JP) .................................. 2007-070663

(51) Int. Cl.
*A61B 5/053* (2006.01)

(52) U.S. Cl.
CPC .................................. *A61B 5/0537* (2013.01)

(58) Field of Classification Search
CPC .................................................... A61B 5/0537
USPC ................................................. 600/547, 382
See application file for complete search history.

(56) References Cited

U.S. PATENT DOCUMENTS

| | | | |
|---|---|---|---|
| 6,978,170 B1 | 12/2005 | Onda et al. | |
| 7,068,827 B2 | 6/2006 | Jeong et al. | |
| 8,099,160 B2 * | 1/2012 | Kanai et al. | 600/547 |
| 8,150,507 B2 * | 4/2012 | Hamaguchi et al. | 600/547 |
| 2004/0077969 A1 | 4/2004 | Onda et al. | |
| 2004/0125995 A1 | 7/2004 | Jeong et al. | |

(Continued)

FOREIGN PATENT DOCUMENTS

| | | |
|---|---|---|
| CN | A-1732845 | 2/2006 |
| JP | A-11-123182 | 5/1999 |

(Continued)

OTHER PUBLICATIONS

Merriam-Webster.com, Abdomen—Definition and More, downloaded Sep. 2, 2014, 2 pages.*

(Continued)

*Primary Examiner* — Lee S Cohen
*Assistant Examiner* — Emily Lloyd
(74) *Attorney, Agent, or Firm* — Oliff PLC

(57) ABSTRACT

A visceral fat measurement device includes a first electrode pair and a second electrode pair to be arranged in a body axis direction at a back surface of an abdomen of a subject; a current generation unit for flowing current between electrodes of the first electrode pair; a potential difference detection unit for detecting a potential difference between electrodes of the second electrode pair current is flowed between the electrodes of the first electrode pair; and a visceral fat mass calculation part for calculating visceral fat mass of the subject based on the detected potential difference between the electrodes of the second electrode pair.

10 Claims, 4 Drawing Sheets

(56) References Cited

U.S. PATENT DOCUMENTS

| | | |
|---|---|---|
| 2005/0059903 A1 | 3/2005 | Izumi |
| 2006/0025701 A1 | 2/2006 | Kasahara |
| 2006/0224080 A1 | 10/2006 | Oku et al. |
| 2007/0038140 A1 | 2/2007 | Masuo et al. |

FOREIGN PATENT DOCUMENTS

| | | |
|---|---|---|
| JP | A-2001-252257 | 9/2001 |
| JP | A-2002-369806 | 12/2002 |
| JP | A-2004-135698 | 5/2004 |
| JP | A-2005-81068 | 3/2005 |
| JP | A-2005-118148 | 5/2005 |
| JP | A-2006-61677 | 3/2006 |
| JP | A-2007-14664 | 1/2007 |
| RU | 2 103 913 C1 | 2/1998 |
| RU | 2 251 387 C1 | 1/2004 |

OTHER PUBLICATIONS

Jan. 18, 2011 Decision on Grant issued in Russian Patent Application No. 2009138330 (with translation).

Sep. 3, 2012 Office Action issued in German Patent Application No. 11 2008 000 629.6 w/translation.

\* cited by examiner

VISCERAL FAT MEASUREMENT DEVICE

TECHNICAL FIELD

The present invention relates to a visceral fat measurement device, in particular, to a visceral fat measurement device for measuring a visceral fat mass of a subject by detecting a potential difference between electrodes arranged on a back surface of an abdomen of the subject.

BACKGROUND ART

A visceral fat mass is conventionally measured using an abdomen tomographic image obtained by an X-ray CT (Computed Tomography). Thus, a problem in that the visceral fat mass can only be measured in medical institutions with an X-ray CT facility arises. An abdomen tomographic image similar to that of the X-ray CT can be photographed with MRI (Magnetic Resonance Imaging), but a large facility is still necessary.

In order to solve such a problem, a device for measuring the visceral fat mass without requiring a large facility is proposed. For example, Japanese Unexamined Patent Publication No. 2002-369806 (Patent Document 1) discloses a first device described below. The first device includes: a first electrode group including one or more electrodes, which position of arrangement on an abdominal surface of a human body is determined with a position of umbilicus of the human body as a reference; a second electrode group including one or more electrodes arranged on a back surface of the human body; a third electrode including two or more electrodes arranged at a position of substantially the middle of the first electrode group and the second electrode group on the surface of the human body; and a controller for flowing current between one electrode selected from the first electrode group and one electrode selected from the second electrode group, measuring the voltage generated between the two electrodes of the third electrode, and calculating the fat mass of the abdomen of the human body based on the measured voltage value.

Furthermore, Patent Document 1 discloses a second device described below. The second device includes: a first electrode group including one or more electrodes, which position of arrangement on the abdominal surface of the body to be measured is determined with the position of umbilicus of the body to be measured as a reference; a second electrode group including three or more electrodes arranged on the back surface of the body to be measured; measurement means for flowing current between two electrodes selected from the second electrode group, and measuring the voltage generated between one electrode selected from the first electrode group and one electrode selected from the second electrode group; and calculating means for calculating the fat mass of the abdomen of the body to be measured based on the voltage value.

[Patent Document 1] Japanese Unexamined Patent Publication No. 2002-369806

DISCLOSURE OF THE INVENTION

Problems to be Solved by the Invention

In the first device described in Patent Document 1, a current is flowed between an abdominal surface and a back surface of a human body to measure a voltage between electrodes of a third electrode group. A visceral fat mass is calculated assuming that the measured voltage is a value correlated with the visceral fat mass. In the second device described in Patent Document 1, the current is flowed between the electrodes arranged on the abdominal surface of the human body and the electrodes arranged on the back surface to measure the voltage between the abdominal surface and the back surface of the human body. The visceral fat mass is calculated assuming that the measured voltage is a value correlated with a subcutaneous fat mass.

However, in the first device and the second device described in Patent Document 1, the voltage measured to calculate the visceral fat mass is influenced by all of the subcutaneous fat, visceral fat, and lean body (muscles, bones, internal organs and the like of human body), and thus the visceral fat mass may not be accurately measured.

Therefore, it is an object of the present invention to provide a visceral fat measurement device capable of accurately measuring the visceral fat mass.

Means for Solving the Problems

In accordance with one aspect of the invention, a visceral fat measurement device includes: a first electrode pair and a second electrode pair to be respectively arranged in a body axis direction at a back surface of an abdomen of a subject; a current generation unit for flowing current between electrodes of the first electrode pair; a potential difference detection unit for detecting a potential difference between electrodes of the second electrode pair when current is flowed between the electrodes of the first electrode pair; and a visceral fat mass calculation part for calculating a visceral fat mass of the subject based on the detected potential difference between the electrodes of the second electrode pair.

Preferably, the visceral fat measurement device further includes: a third electrode pair and a fourth electrode pair to be respectively arranged in the body axis direction at a front surface of the abdomen of the subject; wherein the current generation unit selectively flows current between the electrodes of the first electrode pair and between electrodes of the third electrode pair; the potential difference detection unit detects a potential difference between the electrodes of the second electrode pair when current is flowed between the electrodes of the first electrode pair, and a potential difference between electrodes of the fourth electrode pair when current is flowed between the electrodes of the third electrode pair; and the visceral fat mass calculation part calculates the visceral fat mass of the subject based on the detected potential difference between the electrodes of the second electrode pair and the detected potential difference between the electrodes of the fourth electrode pair.

Preferably, the second electrode pair is arranged in the body axis direction spaced apart from an axis passing through the electrodes of the first electrode pair at the back surface of the abdomen of the subject.

Preferably, each electrode of the second electrode pair and the corresponding electrode of the first electrode pair are arranged in a line in a direction substantially perpendicular to the body axis.

Preferably, the second electrode pair is arranged on an axis passing through the electrodes of the first electrode pair at the back surface of the abdomen of the subject.

More preferably, the second electrode pair is arranged on the axis passing through the electrodes of the first electrode pair and is arranged at a position sandwiched by the first electrode pair at the back surface of the abdomen of the subject.

Preferably, the visceral fat measurement device further includes: a fifth electrode pair to be arranged at a pair of different sites distant from the abdomen of the subject or a first site and a second site at positions sandwiching the abdomen of the subject; wherein the current generation unit selectively flows current between the electrodes of the first electrode pair and electrodes of the fifth electrode pair; the potential difference detection unit detects a potential difference between the electrodes of the second electrode pair when current is flowed between the electrodes of the first electrode pair and the detected potential difference between the electrodes of the second electrode pair when current is flowed between the electrodes of the fifth electrode pair; and the visceral fat mass calculation part calculates the visceral fat mass of the subject based on the potential difference between the electrodes of the second electrode pair detected when current is flowed between the electrodes of the first electrode pair, and the potential difference between the electrodes of the second electrode pair detected when current is flowed between the electrodes of the fifth electrode pair.

More preferably, the first site includes an upper limb, and the second site includes a lower limb.

Preferably, the visceral fat measurement device further includes: a sixth electrode pair and a seventh electrode pair to be arranged in the body axis direction at the back surface of the abdomen of the subject; wherein the current generation unit selectively flows current between the electrodes of the first electrode pair and between electrodes of the sixth electrode pair; the potential difference detection unit detects a potential difference between electrodes of the second electrode pair, the sixth electrode pair, or the seventh electrode pair when current is flowed between the electrodes of the first electrode pair, and a potential difference between electrodes of the first electrode pair, the second electrode pair, or the seventh electrode pair when current is flowed between the electrodes of the sixth electrode pair; and the visceral fat mass calculation part calculates the visceral fat mass of the subject based on the potential difference between the electrodes detected when current is flowed between the electrodes of the first electrode pair, and the potential difference between the electrodes detected when current is flowed between the electrodes of the sixth electrode pair.

Preferably, the visceral fat mass calculation part calculates the visceral fat mass of the subject based on the detected potential difference between the electrodes of the second electrode pair and physical information of the subject.

More preferably, the physical information includes an abdominal width and an abdominal thickness of the subject.

Preferably, the visceral fat measurement device further includes: an impedance calculating section for calculating an impedance of the subject corresponding to between the electrodes of the first electrode pair based on the detected potential difference between the electrodes of the second electrode pair; wherein the visceral fat mass calculation part calculates the visceral fat mass of the subject based on the calculated impedance.

Effect of the Invention

According to the present invention, a visceral fat mass can be accurately measured.

DESCRIPTION OF THE REFERENCE SYMBOLS

Figure 1:
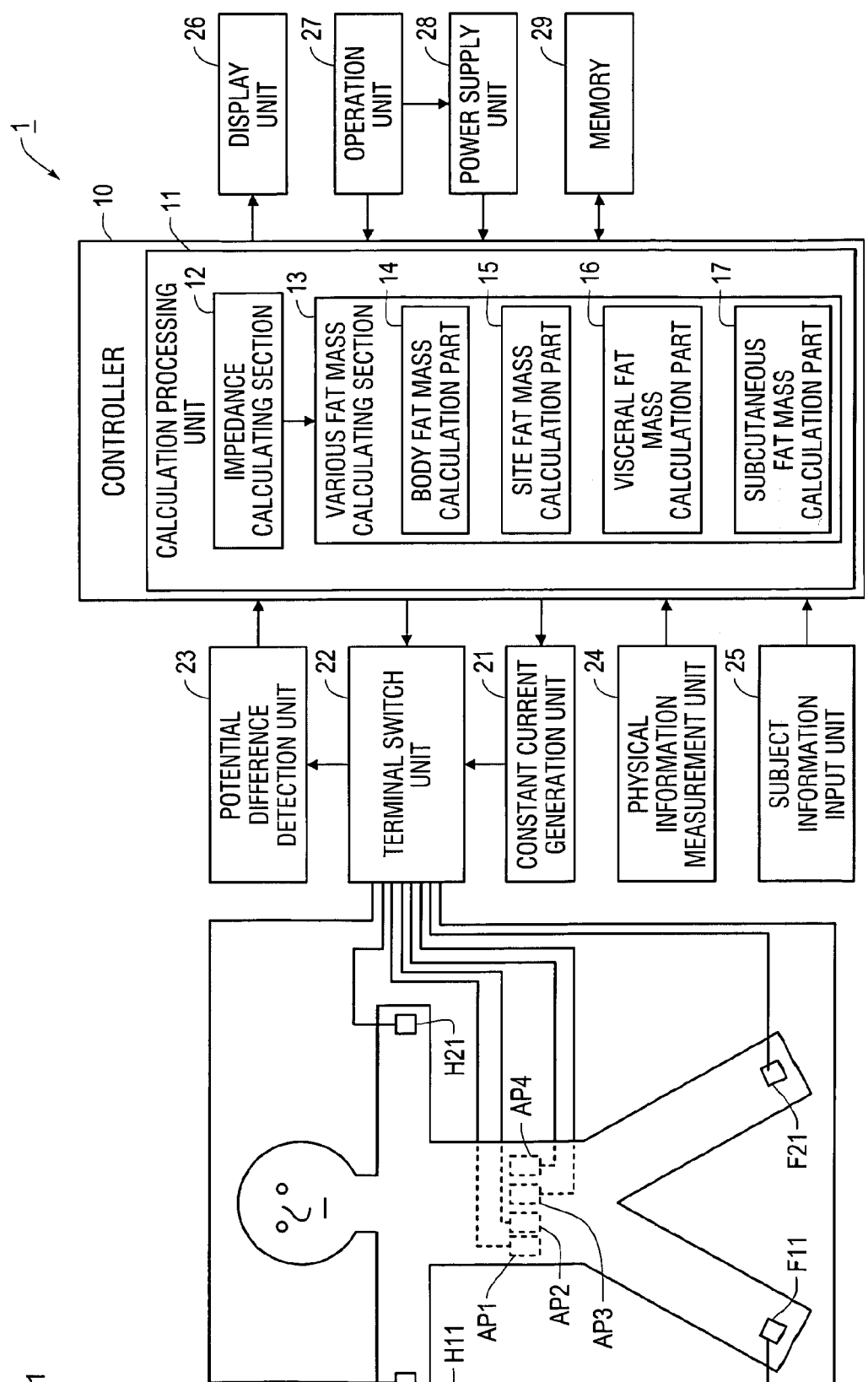
FIG. 1 is a function block diagram of a body fat measurement device according to a first embodiment of the present invention.

1 Body fat measurement device
10 Controller
11 Calculation processing unit
12 Impedance calculating section
13 Various fat mass calculating section
14 Body fat mass calculation part
15 Site fat mass calculation part
16 Visceral fat mass calculation part
17 Subcutaneous fat mass calculation part
21 Constant current generation unit
22 Terminal switch unit
23 Potential difference detection unit
24 Physical information measurement unit
25 Subject information input unit
26 Display unit
27 Operation unit
28 Power supply unit
29 Memory
31, 32 Electrode sheet
AP1 to AP8 Abdominal electrode pair
H11, H21 Upper limb electrode
F11, F21 Lower limb electrode
A11 to A18, A21 to A28 Abdominal electrode

BEST MODE FOR CARRYING OUT THE INVENTION

An embodiment of the present invention will be described with reference to the drawings. In the figures, the same reference numerals are denoted for the same or corresponding portions, and descriptions thereof will not be repeated.

In an embodiment of the present invention described below, description will be made illustrating a body fat measurement device configured to be able to measure not only a visceral fat mass, but also a fat mass of the entire body and a fat mass of specific site of the body (fat mass of upper limb and lower limb, fat mass of trunk, subcutaneous fat mass at abdomen and the like). In other words, the "body fat measurement device" includes a "visceral fat measurement device".

Note that the "abdomen" is a portion excluding a chest of the trunk. A "site distant from the abdomen" includes the upper limb including upper arm, forearm, wrist, and fingers, the chest distant by greater than or equal to a predetermined distance (e.g., about 10 cm) from a diaphragm, an upper body including shoulder, neck, and head, and the lower limb including thigh, lower leg, ankle, and toes. A "body axis" is an axis in a direction substantially perpendicular to a transverse section of an abdomen of a subject. A "front surface of the abdomen" includes a portion that is visible when the subject is observed from the front of the abdomen of the subject. For example, it includes a portion that is visible when the subject is observed from an umbilicus side along an axis passing through the umbilicus and a backbone of the subject and being perpendicular to the body axis of the subject of the abdomen of the subject. A "back surface of the abdomen" includes a portion that is visible when the subject is observed from the back of the abdomen of the subject. For example, it includes a portion that is visible when the subject is observed from the backbone side along an axis passing through the umbilicus and the backbone of the subject and being perpendicular to the body axis of the subject of the abdomen of the subject.

<First Embodiment>

FIG. 1 is a function block diagram of a body fat measurement device according to a first embodiment of the present invention. First, a configuration of the body fat measurement device will be described with reference to FIG. 1.

With reference to FIG. 1, a body fat measurement device 1 mainly includes a controller 10, a constant current generation unit 21, a terminal switch unit 22, a potential difference detection unit 23, a physical information measurement unit 24, a subject information input unit 25, a display unit 26, an operation unit 27, a power supply unit 28, a memory 29, and a plurality of electrodes. The controller 10 includes a calculation processing unit 11.

The body fat measurement device 1 includes abdominal electrode pairs AP1 to AP4 attached to the back surface of the abdomen of the subject, upper limb electrodes H11 and H21 attached to the upper limb of the subject, and lower limb electrodes F11 and F21 attached to the lower limb of the subject as the plurality of electrodes.

The controller 10 is configured by a CPU (Central Processor Unit), for example, and performs an overall control of the body fat measurement device 1. Specifically, the controller 10 sends a command to various types of function blocks, and performs various types of calculation processing based on the obtained information. Various types of calculation processing are performed by the calculation processing unit 11 arranged in the controller 10.

The abdominal electrode pairs AP1 to AP4 are respectively attached to the surface of the back surface of the abdomen of the subject in the body axis direction. The upper limb electrodes H11 and H21 are suitably attached to a surface of a wrist of a right hand and a surface of a wrist of a left hand, respectively. The lower limb electrodes F11 and F21 are suitably attached to a surface of an ankle of a right foot and a surface of an ankle of a left foot, respectively. The abdominal electrode pairs AP1 to AP4, the upper limb electrodes H11 and H21, and the lower limb electrodes F11 and F21 are electrically connected to the terminal switch unit 22.

The terminal switch unit 22 is configured, for example, by a plurality of relay circuits or the like. The terminal switch unit 22 electrically connects a specific electrode pair selected from the plurality of electrodes and the constant current generation unit 21, and electrically connects a specific electrode pair selected from the plurality of electrodes and the potential difference detection unit 23 based on a command received from the controller 10. The electrode pair electrically connected to the constant current generation unit 21 by the terminal switch unit 22 functions as a constant current application electrode pair, and the electrode pair electrically connected to potential difference detection unit 23 by the terminal switch unit 22 functions as a potential difference detection electrode pair. The electrical connection by the terminal switch unit 22 is switched variously during the measurement operation.

The constant current generation unit 21 generates a constant current based on the command received from the controller 10, and supplies the generated constant current to the terminal switch unit 22. The constant current generation unit 21 supplies, for example, a high frequency current (e.g., 50 kHz, 500 µA) suitably used to measure body composition information. The constant current is thereby applied to the subject through the electrode pair electrically connected with the constant current generation unit 21 by the terminal switch unit 22, that is, the constant current application electrode pair.

The potential difference detection unit 23 detects potential difference between the electrodes of the electrode pair electrically connected with the potential difference detection unit 23 by the terminal switch unit 22, that is, the potential difference detection electrode pair, and outputs the detected potential difference to the control unit 10. The potential difference between the electrodes of the potential difference detection electrode pair in a state the constant current is applied to the subject is thereby detected.

The physical information measurement unit 24 and the subject information input unit 25 are units for obtaining the subject information used in the calculation processing performed in the calculation processing unit 11 of the controller 10. In this case, the subject information means information related to the subject, and includes at least one of age, sex, physical information and the like. The physical information is the information related to a size at a specific site of the body of the subject, and for example, includes information including at least one of a waist length (abdominal peripheral length), an abdominal width, an abdominal thickness and the like, and information such as height and weight. The physical information measurement unit 24 is a unit for automatically measuring the physical information of the subject, and outputs the measured physical information to the controller 10. The subject information input unit 25 is a unit for inputting the subject information, and outputs the inputted subject information to the controller 10.

In the function block diagram shown in FIG. 1, a case where both the physical information measurement unit 24 and the subject information input unit 25 are arranged in the body fat measurement device 1 is shown, but the physical information measurement unit 24 and the subject information input unit 25 are not necessarily essential configurations. Whether or not to arrange the physical information measurement unit 24 and/or the subject information input unit 25 is appropriately selected based on the type of subject information used in the calculation processing performed in the calculation processing unit 11 of the controller 10. Of the subject information, the physical information may be automatically measured with the physical information measurement unit 24, or the subject him/herself may input the physical information at the subject information input unit 25.

The calculation processing unit 11 includes an impedance calculating section 12 and various fat mass calculating section 13. The impedance calculating section 12 calculates various types of impedances based on a current value of the constant current generated by the constant current generation unit 21, and the potential difference information detected at the potential difference detection unit 23 and received by the controller 10.

The various fat mass calculating section 13 calculates various fat masses based on the impedance information obtained by the impedance calculating section 12, and the subject information received from the physical information measurement unit 24 and/or the subject information input unit 25. The various fat mass calculating section 13 includes at least one of the body fat mass calculation part 14 for calculating the body fat mass of the entire body of the subject, a site fat mass calculation part 15 for calculating the fat mass of the specific site of the body of the subject, a visceral fat calculation part 16 for calculating the visceral fat mass of the subject, and a subcutaneous fat mass calculation part 17 for calculating the subcutaneous fat mass at the abdomen of the subject. The body fat mass calculation part 14 and the subcutaneous fat mass calculation part 17 may be included in the visceral fat mass calculation part 16.

The display unit 26 displays information of various fat masses calculated in the calculation processing unit 11. An LCD (Liquid Crystal Display), for example, can be used for the display unit 26. The fat mass displayed at the display unit 26 may be the body fat mass of the entire body of the subject, the fat mass of the specific site of the body of the subject, the visceral fat mass, the subcutaneous fat mass at the abdomen and the like. The fat mass refers to an index indicating the fat mass such as fat weight, fat area, fat volume, and fat level, and in particular, the visceral fat mass refers to not only the visceral fat weight, but to at least one of the visceral fat area, the visceral fat volume, and the visceral fat level.

The operation unit 27 is a unit for the subject to input a command to the body fat measurement device 1, and is configured by keys and the like that can be pushed by the subject.

The power supply unit 28 is a unit for supplying power to the controller 10 and the like, and includes an internal power supply such as a battery and an external power supply such as a commercial power supply.

The memory 29 is a unit storing various types of data and programs related to the body fat measurement device 1, and stores, for example, the subject information, the calculated visceral fat mass which are described above, and the body fat measurement program for executing the body fat measurement process which is described below.

One example of the calculation process performed in the body fat measurement device 1 according to the first embodiment of the present invention will now be described. As described above, the body fat measurement device 1 according to the first embodiment of the present invention can measure various fat masses in the various fat mass calculating section 13, but a calculation process performed when calculating the visceral fat area serving as an index indicating the visceral fat mass will be described below.

With reference to FIG. 1, the impedance calculating section 12 calculates two types of impedances based on the value of the current generated in the constant current generation unit 21 and the potential difference detected in the potential difference detection unit 23. One of the two types of impedances is an impedance (hereinafter also referred to as impedance Zt) reflecting the fat free mass at the abdomen of the subject. The other impedance is an impedance (hereinafter also referred to as impedance Zs) reflecting the subcutaneous fat mass at the abdomen of the subject.

The visceral fat mass calculation part 16 calculates the visceral fat mass of the subject such as the visceral fat area (unit: $cm^2$) based on the calculated two types of impedances Zt and Zs, and the physical information (waist length) of the subject. Specifically, a visceral fat area Sv is calculated by the following equation (1) expressing the relationship of the two types of impedances Zt and Zs and the waist length of the subject, and the visceral fat area.

$$Sv = a \times W^2 - b \times (1/Zt) - c \times W \times Zs - d \quad (1)$$

(where, a, b, c, and d are coefficients; and W is waist length)

The subcutaneous fat mass calculation part 17 calculates the subcutaneous fat mass of the subject such as the subcutaneous fat area (unit: $cm^2$) based on the calculated impedance Zs and the physical information (waist length) of the subject. Specifically, a subcutaneous fat area Ss is calculated by the following equation (2) expressing the relationship of the impedance Zs and the waist length of the subject, and the subcutaneous fat area.

$$Ss = e \times W \times Zs + f \quad (2)$$

(where, e and f are coefficients; and W is waist length)

When calculating the body fat mass of the entire body of the subject, the body fat mass calculation part 14 calculates the fat free mass FFM (unit: kg) based on the calculated impedance Zt and one piece of information (e.g., height) contained in the physical information of the subject. Specifically, the fat free mass FFM is calculated by the following equation (3) expressing the relationship of the impedance Zt and the height of the subject, and the fat free mass.

$$FFM = i \times H^2/Zt + j \quad (3)$$

(where i and j are coefficients; and H is height)

The coefficients in each of the above equations (1), (2), and (3) are defined by a regression equation based on the measurement result of the MRI. The coefficients in each equation (1), (2), and (3) may be defined by age and/or sex.

The body fat mass calculation part 14 calculates the body fat mass of the subject such as body fat percentage (%) based on the calculated impedance Zt and at least one piece of information (e.g., weight) contained in the subject information. Specifically, for example, the body fat percentage is calculated by the following equation (4) based on the fat free mass FFM and the weight of the subject.

$$\text{Body fat percentage} = (Wt - FFM)/Wt \times 100 \quad (4)$$

(where, Wt is weight)

Figure 2:
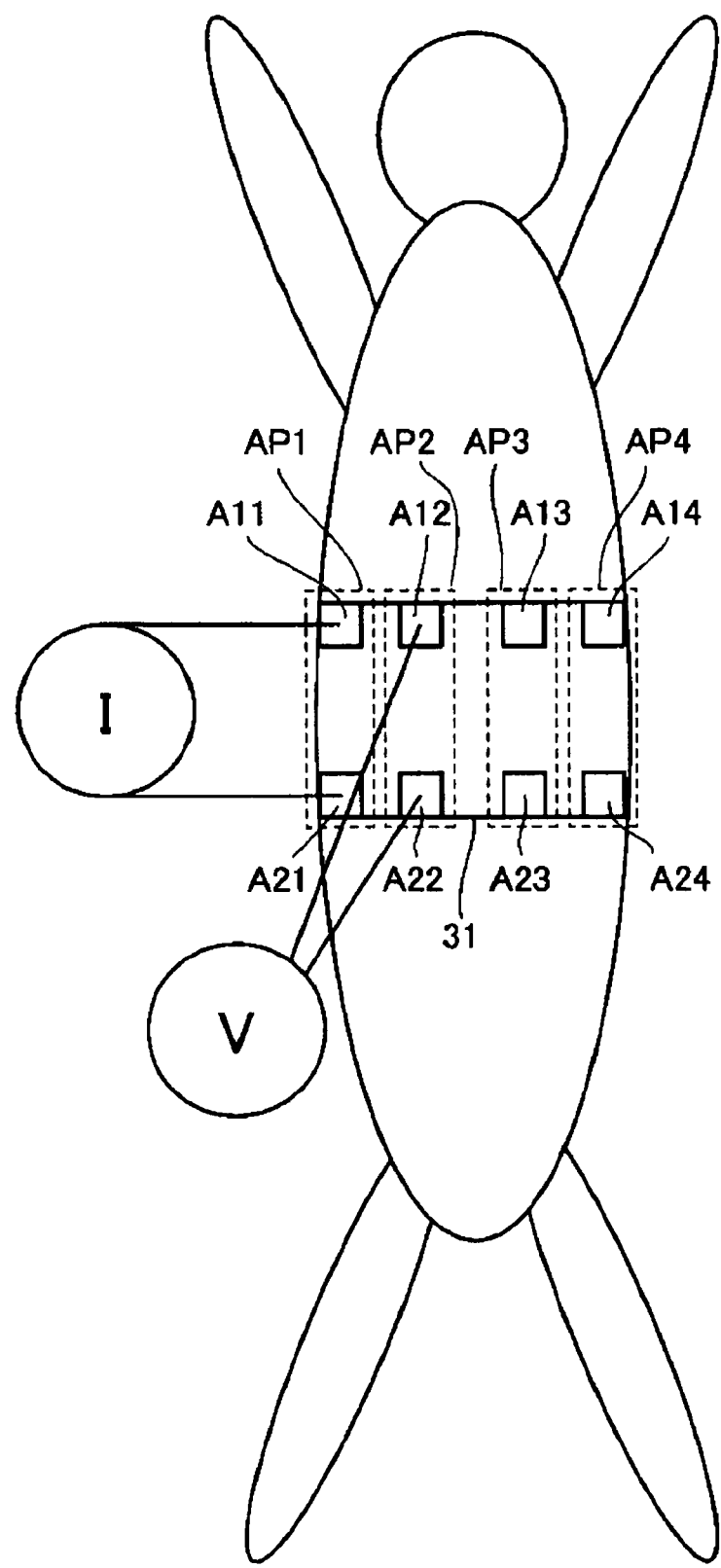
FIG. 2 is a view showing an arrangement example of electrodes in the body fat measurement device according to the first embodiment of the present invention.

FIG. 2 is a view showing an arrangement example of the electrodes in the body fat measurement device according to the first embodiment of the present invention. In FIG. 2, a state in which four pairs of electrodes are arranged is shown.

With reference to FIG. 2, the body fat measurement device 1 includes an electrode sheet 31. The electrode sheet 31 has the abdominal electrode pairs AP1, AP2, AP3, and AP4 and the sheet material integrally formed. The abdominal electrode pair AP1 includes abdominal electrodes A11 and A21. The abdominal electrode pair AP2 includes abdominal electrodes A12 and A22. The abdominal electrode pair AP3 includes abdominal electrodes A13 and A23. The abdominal electrode pair AP4 includes abdominal electrodes A14 and A24.

The abdominal electrode pairs AP1, AP2, AP3, and AP4 are respectively arranged in the body axis direction at the back surface of the abdomen of the subject, and are arranged spaced apart from each other in a direction substantially perpendicular to the body axis. For example, the abdominal electrode pair AP2 is arranged with a predetermined distance from an axis passing through the abdominal electrodes A11 and A21 of the abdominal electrode pair AP1.

Each inter-electrode distance of the abdominal electrode pairs AP1, AP2, AP3, and AP4 is substantially equal. For example, the distance between the abdominal electrodes A11 and A21 of the abdominal electrode pair AP1 and the distance between the abdominal electrodes A12 and A22 of the abdominal electrode pair AP2 are substantially equal. Each electrode of the abdominal electrode pairs AP1, AP2, AP3, and AP4 is arranged aligned in a direction substantially perpendicular to the body axis with the electrode of another corresponding electrode pair. In other words, the abdominal electrodes A11, A12, A13, and A14 are arranged in a line in a direction substantially perpendicular to the body axis. The abdominal electrodes A21, A22, A23, and A24 are arranged in a line in a direction substantially perpendicular to the body axis.

The abdominal electrode pairs AP1, AP2, AP3, and AP4 may be arranged in a line in the body axis direction. In other words, the abdominal electrode pairs AP2, AP3, and AP4 may be arranged on an axis passing through the abdominal electrodes A11 and A21 of the abdominal electrode pair AP1.

A certain abdominal electrode pair may be arranged at a position sandwiching another abdominal electrode pair. For example, the abdominal electrode pairs AP1 and AP2 are arranged in a line in the body axis direction and the abdominal electrode pair AP1 is arranged at a position sandwiching the abdominal electrode pair AP2. In addition, the abdominal electrode pairs AP3 and AP4 may be arranged in a line in the body axis direction and the abdominal electrode pair AP3 may be arranged at a position sandwiching the abdominal electrode pair AP4.

The constant current generation unit 21 flows current between the electrodes of the electrode pair (hereinafter also referred to as current electrode pair) electrically connected with the constant current generation unit 21 by the terminal switch unit 22.

The potential difference detection unit 23 detects the potential difference between the electrodes of the electrode pair (hereinafter also referred to as voltage electrode pair) electrically connected with the potential difference detection unit 23 by the terminal switch unit 22.

The visceral fat mass calculation part 16 calculates the visceral fat mass of the subject based on the potential difference between the electrodes of the voltage electrode pair detected by the potential difference detection unit 23.

[Operation of Body Fat Measurement Device]

An operation of when the body fat measurement device according to the first embodiment of the present invention measures the visceral fat mass will now be described.

Figure 3:
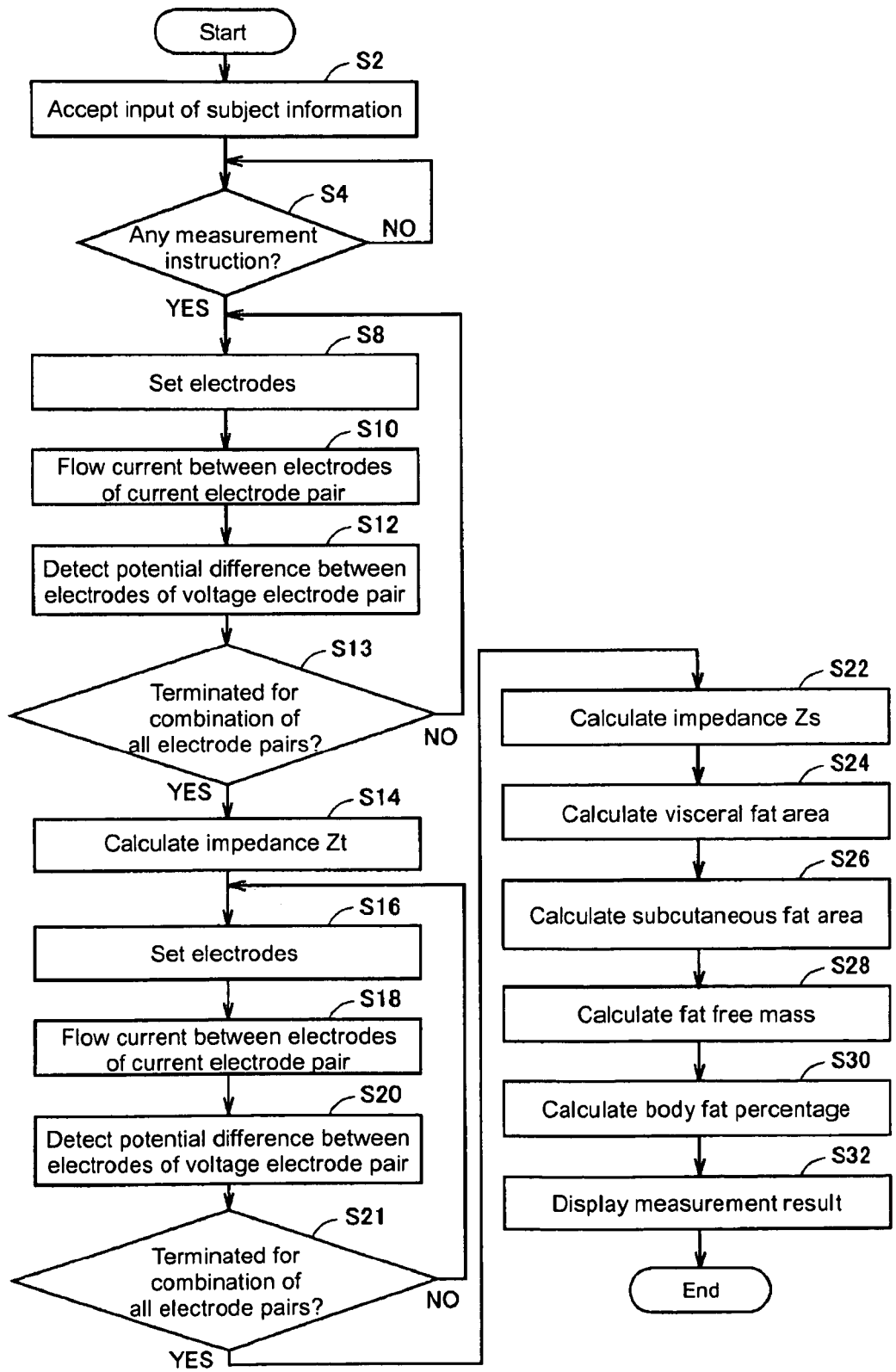
FIG. 3 is a flowchart defined with operation procedures of when the body fat measurement device according to the first embodiment of the present invention and a second embodiment of the present invention measures a visceral fat mass.

FIG. 3 is a flowchart defined with the operation procedures of when the body fat measurement device according to the first embodiment of the present invention measures the visceral fat mass. The process shown in the flowchart of FIG. 3 is stored in the memory 29 as a program in advance, where the controller 10 reads out and executes the program to realize a function of the visceral fat measurement process.

With reference to FIG. 3, the controller 10 accepts the input of the subject information containing the physical information (waist length) (step S2). The accepted subject information is temporarily saved in the memory 29, for example.

The controller 10 determines whether or not an instruction to start the measurement is made (step S4). The controller 10 waits until the instruction to start the measurement is made (NO in step S4). The controller 10 sets the electrode (step S8) when detecting the instruction to start the measurement (YES in step S4).

More specifically, the controller 10 first performs the calculation process of the impedance Zt. In other words, the controller 10 selects, for example, a pair of upper limb electrode H11 and lower limb electrode F11 and a pair of upper limb electrode H21 and lower limb electrode F21 as the current electrode pairs, and selects the abdominal electrode pair AP1 as the voltage electrode pair. The terminal switch unit 22 electrically connects the pair of upper limb electrode H11 and lower limb electrode F11 and the pair of upper limb electrode H21 and lower limb electrode F21 with the constant current generation unit 21, and electrically connects the abdominal electrode pair AP1 with the potential difference detection unit 23 based on the control of the controller 10 (step S8). Here, the terminal switch unit 22 cuts the electrical connection of the non-selected electrode and the constant current generation unit 21 and the potential difference detection unit 23 based on the control of the controller 10.

The constant current generation unit 21 flows current in the direction from the upper limb to the lower limb based on the control of the controller 10. For example, the constant current generation unit 21 flows current from the upper limb electrode H11 and the upper limb electrode H21 to the lower limb electrode F11 and the lower limb electrode F21 (step S10). In this case, the terminal switch unit 22 preferably has a configuration of short circuiting the upper limb electrode H11 and the upper limb electrode H21 and short circuiting the lower limb electrode F11 and the lower limb electrode F21. The constant current generation unit 21 and the terminal switch unit 22 may have a configuration of flowing current from either one of the upper limb electrodes H11 and H21 to either one of the lower limb electrodes F11 and F21.

In this state, the potential difference detection unit 23 detects the potential difference between the abdominal electrodes A11 and A21 of the abdominal electrode pair AP1 based on the control of the controller 10 (step S12).

The controller 10 selects the abdominal electrode pairs AP2, AP3, and AP4 as the voltage electrode pair in order. That is, the terminal switch unit 22 electrically connects the abdominal electrode pairs AP2, AP3, and AP4 with the potential difference detection unit 23 in order based on the control of the controller 10 (step S8). The potential difference detection unit 23 then detects the potential difference between the electrodes of each of the abdominal electrode pairs AP2, AP3, and AP4 in order based on the control of the controller 10 (step S12).

When the detection of the potential difference is terminated for the combination of all electrode pairs, or when the detection of the potential difference between the electrodes of each of the abdominal electrode pairs AP1, AP2, AP3, and AP4 is terminated (YES in step S13), the impedance calculating section 12 calculates impedances Zt1 to Zt4 based on the value of the current flowed by the constant current generation unit 21 and each potential difference detected by the potential difference detection unit 23 (step S14). The values of the impedances Zt1 to Zt4 calculated by the impedance calculating section 12 are temporarily saved in the memory 29, for example.

The controller 10 then performs the calculation process of the impedance Zs.

In other words, the controller 10 selects the abdominal electrode pair AP1 as the current electrode pair, and selects the abdominal electrode pair AP2 as the voltage electrode pair. The terminal switch unit 22 electrically connects the abdominal electrode pair AP1 with the constant current generation unit 21 and electrically connects the abdominal electrode pair AP2 with the potential difference detection unit 23 based on the control of the controller 10 (step S16). Here, the terminal switch unit 22 selectively electrically connects each abdominal electrode pair with the potential difference detection unit 23 and cuts the electrical connection of the non-selected abdominal electrode pair, the upper limb electrode and the lower limb electrode with the constant current generation unit 21 and the potential difference detection unit 23 based on the control of the controller 10.

The constant current generation unit 21 flows current between the abdominal electrodes A11 and A21 of the abdominal electrode pair AP1 based on the control of the controller 10 (step S18).

In this state, the potential difference detection unit 23 detects the potential difference between the abdominal electrodes A12 and A22 of the abdominal electrode pair AP2 based on the control of the controller 10 (step S20).

The controller 10 selects the abdominal electrode pairs AP3 and AP4 as the voltage electrode pair in order. That is, the terminal switch unit 22 electrically connects the abdominal electrode pairs AP3 and AP4 with the potential difference detection unit 23 in order based on the control of the controller 10 (step S16). The potential difference detection unit 23 then detects the potential difference between the electrodes of each of the abdominal electrode pairs AP3 and AP4 in order based on the control of the controller 10 (step S20).

The controller 10 then selects the abdominal electrode pair AP2 as the current electrode pair, and selects the abdominal electrode pair AP1 as the voltage electrode pair. In other words, the terminal switch unit 22 electrically connects the abdominal electrode pair AP2 with the constant current generation unit 21 and electrically connects the abdominal electrode pair AP1 with the potential difference detection unit 23 based on the control of the controller 10 (step S16).

The constant current generation unit 21 flows current between the abdominal electrodes A12 and A22 of the abdominal electrode pair AP2 based on the control of the controller 10 (step S18).

In this state, the potential difference detection unit 23 detects the potential difference between the abdominal electrodes A11 and A21 of the abdominal electrode pair AP1 based on the control of the controller 10 (step S20).

The controller 10 selects the abdominal electrode pairs AP3 and AP4 as the voltage electrode pair in order. That is, the terminal switch unit 22 electrically connects the abdominal electrode pairs AP3 and AP4 with the potential difference detection unit 23 in order based on the control of the controller 10 (step S16). The potential difference detection unit 23 then detects the potential difference between the electrodes of each of the abdominal electrode pairs AP3 and AP4 in order based on the control of the controller 10 (step S20).

Similarly, the controller 10 selects the abdominal electrode pairs AP3 and AP4 as the current electrode pair in order, selects the abdominal electrode pair other than the current electrode pairs of the abdominal electrode pairs AP1 to AP4 in order for each of the abdominal electrode pairs AP3 and AP4, and detects the respective potential difference between the electrodes of the voltage electrode pairs (steps S16 to S20).

When application of current and detection of potential difference are terminated with respect to the combination of all electrode pairs (YES in step S21), the impedance calculating section 12 calculates the impedances Zs1 to Zs12 based on the value of the current flowed by the constant current generation unit 21 and each potential difference detected by the potential difference detection unit 23 (step S22). The values of the impedances Zs1 to Zs12 calculated by the impedance calculating section 12 are temporarily saved in the memory 29, for example.

The visceral fat mass calculation part 16 then calculates the visceral fat area Sv based on the physical information (waist length) accepted by the controller 10 in step S2, the impedances Zt1 to Zt4, and the impedances Zs1 to Zs12 (step S24). The visceral fat area Sv is calculated by equation (1). When the body fat measurement device includes four abdominal electrode pairs AP1 to AP4, as in the first embodiment of the present invention, an average value of the four impedances Zt1 to Zt4 is substituted to the impedance Zt of equation (1), and an average value of the twelve impedances Zs1 to Zs12 is substituted to the impedance Zs of equation (1).

The subcutaneous fat mass calculation part 17 calculates the subcutaneous fat area Ss based on the physical information (waist length) accepted by the controller 10 in step S2, and the impedances Zs1 to Zs12 (step S26). The subcutaneous fat area Ss is calculated by equation (2). When the body fat measurement device 1 includes four abdominal electrode pairs AP1 to AP4, as in the first embodiment of the present invention, the average value of the twelve impedances Zs1 to Zs12, for example, is substituted to the impedance Zs of equation (2).

The body fat mass calculation part 14 calculates the fat free mass FFM based on the subject information (e.g., height) inputted in step S2 and the impedances Zt1 to Zt4 (step S28). The fat free mass FFM is calculated by equation (3). When the body fat measurement device 1 includes four abdominal electrode pairs AP1 to AP4, as in the first embodiment of the present invention, the average value of the four impedances Zt1 to Zt4, for example, is substituted to the impedance Zt of equation (3).

The body fat mass calculation part 14 calculates the body fat percentage based on the subject information (weight) inputted in step S2 and the fat free mass FFM calculated in step S28 (step S30). The body fat percentage is calculated from equation (4).

The display unit 26 displays each measurement result based on the control of the controller 10 (step S32).

The body fat measurement device 1 then terminates the body fat measurement process.

Note that a typical value of the impedances Zt1 to Zt4 is about 5 Ω. A typical value of the impedances Zs1 to Zs12 is about 80 Ω.

In the first device and the second device described in Patent Document 1, the voltage measured to calculate the visceral fat mass is influenced by all of the subcutaneous fat, the visceral fat, and the lean body (muscles, bones, internal organs and the like of human body), and thus the visceral fat mass cannot be accurately measured.

However, the body fat measurement device according to the first embodiment of the present invention includes the abdominal electrode pairs AP1 to AP4 respectively arranged in the body axis direction at the back surface of the abdomen of the subject. The potential difference detection unit 23 detects the potential difference between the electrodes of another electrode pair when current is flowed between the electrodes of any one of the electrode pair of the abdominal electrode pairs AP1 to AP4. The visceral fat mass calculation part 16 calculates the visceral fat mass of the subject based on the detected potential difference. With such a configuration, the potential difference correlated only with the subcutaneous fat excluding the influence of the visceral fat and the lean body can be detected, and thus the visceral fat mass can be accurately measured based on the detected potential difference.

Generally, the subcutaneous fat is greater at the back surface of the abdomen rather than at the front surface of the abdomen. Thus, in the body fat measurement device according to the first embodiment of the present invention, the constant current generation unit 21 flows current between the electrodes of the current electrode pair arranged in the body axis direction at the back surface of the abdomen of the subject. The visceral fat mass calculation part 16 then calculates the visceral fat mass based on the potential difference between the electrodes of the voltage electrode pair arranged in the body axis direction at the back surface of the abdomen of the subject. With such a configuration, the potential difference having greater correlation with the subcutaneous fat can be detected, and thus the visceral fat mass can be accurately measured based on the detected potential difference.

Furthermore, according to the configuration as mentioned above, a difference in curvature between the electrodes of the current electrode pair and a difference in curvature between the electrodes of the voltage electrode pair can be further reduced among the subjects having a different shape of the abdomen, that is, a different protruding degree in the direction parallel to the transverse section of the abdomen. A variance in detection range and detection sensitivity of the potential difference among the subjects due to the difference in curvature between the electrodes thus can be reduced. A fluctuation of the potential difference due to a fluctuation of the electrode position in the direction parallel to the transverse section of the abdomen that occurs in breathing can also be reduced. Therefore, the measurement accuracy of the visceral fat mass can be enhanced in the body fat measurement device according to the first embodiment of the present invention.

The subcutaneous fat mass is often even in a direction substantially perpendicular to the body axis direction of the subject, but greatly differs in the body axis direction of the subject. In the body fat measurement device according to the first embodiment of the present invention, the subcutaneous fat mass in the body axis direction of the subject in which variation is large can be measured according to the configuration described above, and thus the visceral fat mass can be accurately measured.

The electrode sheet 31 is difficult to attach if the width in the body axis direction is too large, and the body fat measurement device enlarges. Thus, the distance in the body axis direction between the abdominal electrodes and the number of abdominal electrodes are preferably small to a certain extent. In the body fat measurement device according to the first embodiment of the present invention, the abdominal electrode pairs AP1, AP2, AP3, and AP4 are respectively arranged in the body axis direction at the back surface of the abdomen of the subject, and are arranged apart from each other in a direction substantially perpendicular to the body axis. With such a configuration, the width in the body axis direction of the electrode sheet 31 can be reduced, whereby enhancement of the attachment property and miniaturization of the body fat measurement device can be achieved.

In the body fat measurement device according to the first embodiment of the present invention, a plurality of abdominal electrode pairs AP1, AP2, AP3, and AP4 are arranged, a plurality of impedances Zt and a plurality of impedances Zs are respectively calculated based on the measured potential difference between the electrodes of each electrode pair, and the visceral fat mass is calculated using the respective average value of the impedance Zt and the impedance Zs. With such a configuration, an influence of variation in the distribution of fat and the thickness of fat can be eliminated.

In the body fat measurement device according to the first embodiment of the present invention, the impedance calculating section 12 collectively calculates the impedance after the potential differences corresponding to the combination of all electrode pairs are detected in the flowchart of FIG. 3, but the present invention is not limited thereto. The impedance may be calculated every time the potential difference between the electrodes of the electrode pair is detected. The setting order of the current electrode pair and the voltage electrode pair is not limited to the order shown in the flowchart of FIG. 3. The impedance Zt may be calculated after calculating the impedance Zs.

In the body fat measurement device according to the first embodiment of the present invention, the visceral fat mass calculation part 16 substitutes the average value of the impedances Zt1 to Zt4 to the impedance Zt of equation (1), and substitutes the average value of the impedances Zs1 to Zs12 to the impedance Zs of equation (1) in the flowchart of FIG. 3, but the present invention is not limited thereto. The impedance calculating section 12 calculates the impedance Zt based on the average value of the plurality of potential differences detected when current is flowed between the upper limb electrode and the lower limb electrode. The impedance calculating section 12 may be configured to calculate the impedance Zs based on the average value of the plurality of potential differences detected when current is flowed between the electrodes of the abdominal electrode pair.

The impedance calculating section 12 may be configured to provide a correlation equation for each impedance Zt and impedance Zs and calculate the impedances Zt and Zs. A configuration of selecting a representative value of the impedances Zt and Zs may also be adopted. The representative value is selected based on a predetermined condition such as a maximum value of the plurality of calculated impedances.

Generally, a difference due to a physical constitution of the subject is small regarding the fat free mass. Therefore, not limited to the configuration of calculating the impedance Zt corresponding to the fat free mass based on the potential difference between the electrodes of the abdominal electrode pair when current is flowed between the upper limb electrode and the lower limb electrode as in the body fat measurement device according to the first embodiment of the present invention, the impedance Zt may be saved as a fixed value and the saved impedance Zt may be used to calculate the visceral fat mass.

In the body fat measurement device according to the first embodiment of the present invention, the visceral fat mass is calculated using the waist length as the physical information, but the present invention is not limited thereto, and a horizontal width of the abdomen and a thickness of the abdomen may be used for the physical information instead of the waist length.

In the body fat measurement device according to the first embodiment of the present invention, the visceral fat mass (visceral fat area), the subcutaneous fat mass (subcutaneous fat area), and the body fat mass (body fat percentage) are calculated for the body fat of the subject, but at least the visceral fat mass needs to be calculated. In this case, the subject information obtained by the subject information input unit 25 may be only the physical information (waist length).

Another embodiment of the present invention will be described with reference to the drawings. Note that the same reference numerals are denoted for the same or corresponding portions in the figure, and descriptions thereof will not be repeated.

<Second Embodiment>

The present embodiment relates to a body fat measurement device in which an abdominal electrode pair arranged on the front surface of the abdomen is added. The content other than the content described below is similar to the body fat measurement device according to the first embodiment.

Figure 4:
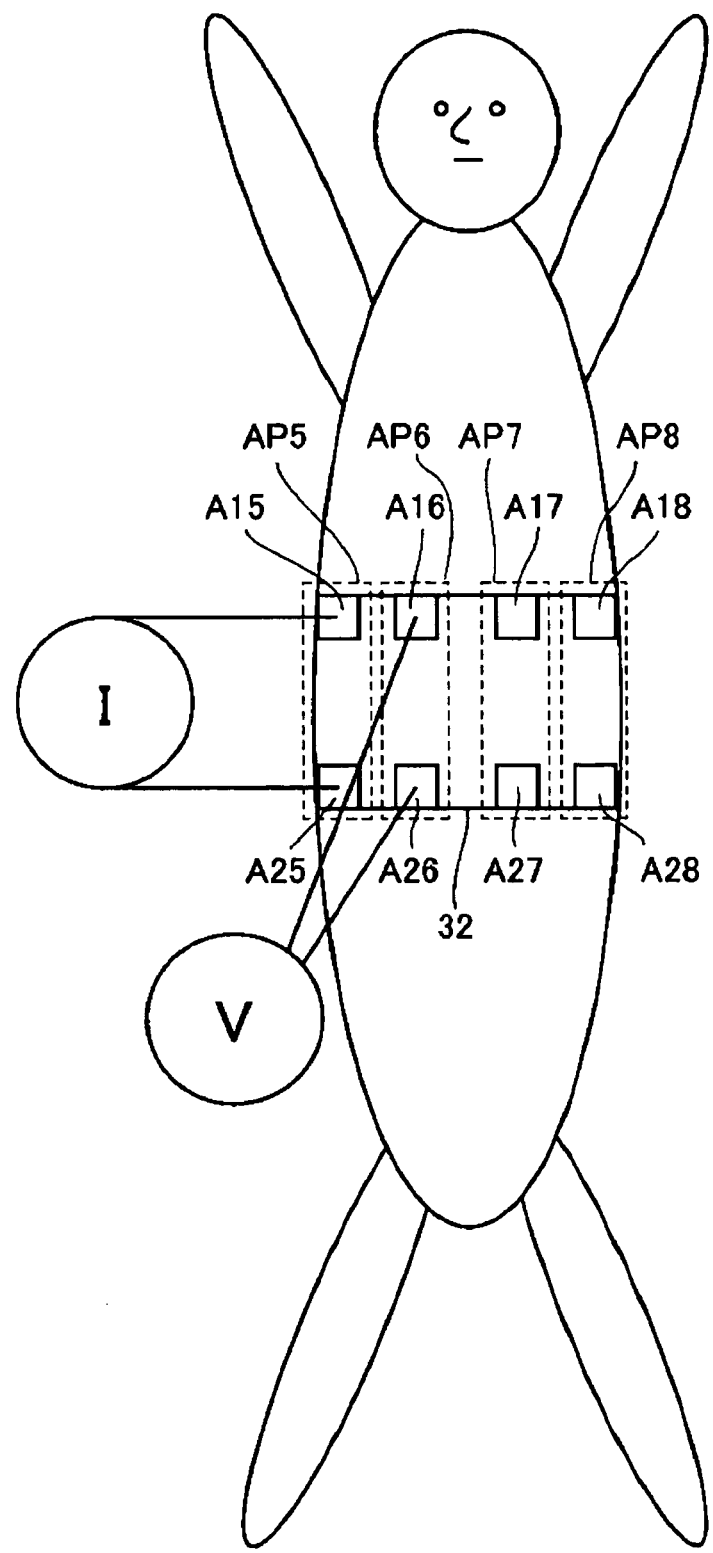
FIG. 4 is a view showing an arrangement example of electrodes in the body fat measurement device according to the second embodiment of the present invention.

FIG. 4 is a view showing an arrangement example of the electrodes in the body fat measurement device according to the second embodiment of the present invention.

With reference to FIG. 4, the body fat measurement device according to the second embodiment of the present invention further includes an electrode sheet 32 compared to the body fat measurement device according to the first embodiment of the present invention. The electrode sheet 32 has the abdominal electrode pairs AP5, AP6, AP7, and AP8 and the sheet material integrally formed. The abdominal electrode pair AP5 includes abdominal electrodes A15 and A25. The abdominal electrode pair AP6 includes abdominal electrodes A16 and A26. The abdominal electrode pair AP7 includes abdominal electrodes A17 and A27. The abdominal electrode pair AP8 includes abdominal electrodes A18 and A28. Note that the electrode sheet 32 and the electrode sheet 31 may be integrally formed or may be separated.

The abdominal electrode pairs AP5, AP6, AP7, and AP8 are respectively arranged in the body axis direction at the front surface of the abdomen of the subject and are arranged spaced apart from each other in a direction substantially perpendicular to the body axis. For example, the abdominal electrode pair AP6 is arranged with a predetermined distance from an axis passing through the abdominal electrodes A15 and A25 of the abdominal electrode pair AP5.

Each inter-electrode distance of the abdominal electrode pairs AP5, AP6, AP7, and AP8 is substantially equal. For example, the distance between the abdominal electrodes A15 and A25 of the abdominal electrode pair AP5 and the distance between the abdominal electrodes A16 and A26 of the abdominal electrode pair AP6 are substantially equal. Each electrode of the abdominal electrode pairs AP5, AP6, AP7, and AP8 is arranged aligned in a direction substantially perpendicular to the body axis with the electrode of another corresponding electrode pair. In other words, the abdominal electrodes A15, A16, A17, and A18 are arranged in a line in a direction substantially perpendicular to the body axis. The abdominal electrodes A25, A26, A27, and A28 are arranged in a line in a direction substantially perpendicular to the body axis.

The abdominal electrode pairs AP5, AP6, AP7, and AP8 may be arranged in a line in the body axis direction. In other words, the abdominal electrode pairs AP6, AP7, and AP8 may be arranged on an axis passing through the abdominal electrodes A15 and A25 of the abdominal electrode pair AP5.

A certain abdominal electrode pair may be arranged at a position sandwiching another abdominal electrode pair. For example, the abdominal electrode pairs AP5 and AP6 are arranged in a line in the body axis direction and the abdominal electrode pair AP5 is arranged at a position sandwiching the abdominal electrode pair AP6. In addition, the abdominal electrode pairs AP7 and AP8 may be arranged in a line in the body axis direction and the abdominal electrode pair AP7 may be arranged at a position sandwiching the abdominal electrode pair AP8.

The constant current generation unit 21 flows current between the electrodes of the electrode pair, that is, the current electrode pair electrically connected with the constant current generation unit 21 by the terminal switch unit 22.

The potential difference detection unit 23 detects the potential difference between the electrodes of the electrode pair, that is, the voltage electrode pair electrically connected with the potential difference detection unit 23 by the terminal switch unit 22.

The visceral fat mass calculation part 16 calculates the visceral fat mass of the subject based on the potential difference between the electrodes of the voltage electrode pair at the back surface of the abdomen detected by the potential difference detection unit 23 and the potential difference between the electrodes of the voltage electrode pair at the front surface of the abdomen detected by the potential difference detection unit 23.

[Operation of Body Fat Measurement Device]

An operation of when the body fat measurement device according to the second embodiment of the present invention measures the visceral fat mass will now be described.

The flowchart defined with the operation procedures of when the body fat measurement device according to the second embodiment of the present invention measures the visceral fat mass is shown in FIG. 3, similar to the body fat measurement device according to the first embodiment of the present invention. The process shown in the flowchart of FIG. 3 is stored in the memory 29 as a program in advance, where the controller 10 reads out and executes the program to realize a function of the visceral fat measurement process.

With reference to FIG. 3, the controller 10 accepts the input of the subject information containing the physical information (waist length) (step S2). The accepted subject information is temporarily saved in the memory 29, for example.

The controller 10 determines whether or not an instruction to start the measurement is made (step S4). The controller 10 waits until the instruction to start the measurement is made (NO in step S4). The controller 10 sets the electrode (step S8) when detecting the instruction to start the measurement (YES in step S4).

More specifically, the controller 10 first performs the calculation process of the impedance Zt. In other words, the controller 10 selects, for example, a pair of upper limb electrode H11 and lower limb electrode F11 and a pair of upper limb electrode H21 and lower limb electrode F21 as the current electrode pairs, and selects the abdominal electrode pair AP1 as the voltage electrode pair. The terminal switch unit 22 electrically connects the pair of upper limb electrode H11 and lower limb electrode F11 and the pair of upper limb electrode H21 and lower limb electrode F21 with the constant current generation unit 21, and electrically connects the abdominal electrode pair AP1 with the potential difference detection unit 23 based on the control of the controller 10 (step S8). Here, the terminal switch unit 22 cuts the electrical connection of the non-selected electrode and the constant current generation unit 21 and the potential difference detection unit 23 based on the control of the controller 10.

The constant current generation unit 21 flows current in the direction from the upper limb to the lower limb based on the control of the controller 10. For example, the constant current generation unit 21 flows current from the upper limb electrode H11 and the upper limb electrode H21 to the lower limb electrode F11 and the lower limb electrode F21 (step S10). In this case, the terminal switch unit 22 preferably has a configuration of short circuiting the upper limb electrode H11 and the upper limb electrode H21 and short circuiting the lower limb electrode F11 and the lower limb electrode F21. The constant current generation unit 21 and the terminal switch unit 22 may have a configuration of flowing current from either one of the upper limb electrodes H11 and H21 to either one of the lower limb electrodes F11 and F21.

In this state, the potential difference detection unit 23 detects the potential difference between the abdominal electrodes A11 and A21 of the abdominal electrode pair AP1 based on the control of the controller 10 (step S12).

The controller 10 selects the abdominal electrode pairs AP2, AP3, AP4, AP5, AP6, AP7, and AP8 as the voltage electrode pair in order. That is, the terminal switch unit 22 electrically connects the abdominal electrode pairs AP2, AP3, AP4, AP5, AP6, AP7, and AP8 with the potential difference detection unit 23 in order based on the control of the controller 10 (step S8). The potential difference detection unit 23 then detects the potential difference between the electrodes of each of the abdominal electrode pairs AP2, AP3, AP4, AP5, AP6, AP7, and AP8 in order based on the control of the controller 10 (step S12).

When the detection of the potential difference is terminated for the combination of all electrode pairs, or when the detection of the potential difference between the electrodes of each of the abdominal electrode pairs AP1, AP2, AP3, AP4, AP5, AP6, AP7, and AP8 herein is terminated (YES in step S13), the impedance calculating section 12 calculates impedances Zt1 to Zt8 based on the value of the current flowed by the constant current generation unit 21 and each potential difference detected by the potential difference detection unit 23 (step S14). The values of the impedances Zt1 to Zt8 calculated by the impedance calculating section 12 are temporarily saved in the memory 29, for example.

The controller 10 then performs the calculation process of the impedance Zs at the back surface of the abdomen.

In other words, the controller 10 selects the abdominal electrode pair AP1 as the current electrode pair, and selects the abdominal electrode pair AP2 as the voltage electrode pair. The terminal switch unit 22 electrically connects the abdominal electrode pair AP1 with the constant current generation unit 21 and electrically connects the abdominal electrode pair AP2 with the potential difference detection unit 23 based on the control of the controller 10 (step S16). Here, the terminal switch unit 22 selectively electrically connects each abdominal electrode pair with the potential difference detection unit 23 and cuts the electrical connection of the non-selected abdominal electrode pair, the upper limb electrode and the lower limb electrode with the constant current generation unit 21 and the potential difference detection unit 23 based on the control of the controller 10.

The constant current generation unit 21 flows current between the abdominal electrodes A11 and A21 of the abdominal electrode pair AP1 based on the control of the controller 10 (step S18).

In this state, the potential difference detection unit 23 detects the potential difference between the abdominal electrodes A12 and A22 of the abdominal electrode pair AP2 based on the control of the controller 10 (step S20).

The controller 10 selects the abdominal electrode pairs AP3 and AP4 as the voltage electrode pair in order. That is, the terminal switch unit 22 electrically connects the abdominal electrode pairs AP3 and AP4 with the potential difference detection unit 23 in order based on the control of the controller 10 (step S16). The potential difference detection unit 23 then detects the potential difference between the electrodes of each of the abdominal electrode pairs AP3 and AP4 in order based on the control of the controller 10 (step S20).

The controller 10 then selects the abdominal electrode pair AP2 as the current electrode pair, and selects the abdominal electrode pair AP1 as the voltage electrode pair. In other words, the terminal switch unit 22 electrically connects the abdominal electrode pair AP2 with the constant current generation unit 21 and electrically connects the abdominal electrode pair AP1 with the potential difference detection unit 23 based on the control of the controller 10 (step S16).

The constant current generation unit 21 flows current between the abdominal electrodes A12 and A22 of the abdominal electrode pair AP2 based on the control of the controller 10 (step S18).

In this state, the potential difference detection unit 23 detects the potential difference between the abdominal electrodes A11 and A21 of the abdominal electrode pair AP1 based on the control of the controller 10 (step S20).

The controller 10 selects the abdominal electrode pairs AP3 and AP4 as the voltage electrode pair in order. That is, the terminal switch unit 22 electrically connects the abdominal electrode pairs AP3 and AP4 with the potential difference detection unit 23 in order based on the control of the controller 10 (step S16). The potential difference detection unit 23 then detects the potential difference between the electrodes of each of the abdominal electrode pairs AP3 and AP4 in order based on the control of the controller 10 (step S20).

Similarly, the controller 10 selects the abdominal electrode pairs AP3 and AP4 as the current electrode pair in order, selects the abdominal electrode pair other than the current electrode pairs of the abdominal electrode pairs AP1 to AP4 in order for each of the abdominal electrode pairs AP3 and AP4, and detects the respective potential difference between the electrodes of the voltage electrode pairs (steps S16 to S20).

The controller 10 then performs the calculation process of the impedance Zs.

In other words, the controller 10 selects the abdominal electrode pair AP5 as the current electrode pair, and selects the abdominal electrode pair AP6 as the voltage electrode pair. The terminal switch unit 22 electrically connects the abdominal electrode pair AP5 with the constant current generation unit 21 and electrically connects the abdominal electrode pair AP6 with the potential difference detection unit 23 based on the control of the controller 10 (step S16). Here, the terminal switch unit 22 selectively electrically connects each abdominal electrode par with the potential difference detection unit 23 and cuts the electrical connection of the non-selected abdominal electrode pair, the upper limb electrode and the lower limb electrode with the constant current generation unit 21 and the potential difference detection unit 23 based on the control of the controller 10.

The constant current generation unit 21 flows current between the abdominal electrodes A15 and A25 of the abdominal electrode pair AP5 based on the control of the controller 10 (step S18).

In this state, the potential difference detection unit 23 detects the potential difference between the abdominal electrodes A16 and A26 of the abdominal electrode pair AP6 based on the control of the controller 10 (step S20).

The controller 10 selects the abdominal electrode pairs APT and AP8 as the voltage electrode pair in order. That is, the terminal switch unit 22 electrically connects the abdominal electrode pairs AP7 and AP8 with the potential difference detection unit 23 in order based on the control of the controller 10 (step S16). The potential difference detection unit 23 then detects the potential difference between the electrodes of each of the abdominal electrode pairs AP7 and AP8 in order based on the control of the controller 10 (step S20).

The controller 10 then selects the abdominal electrode pair AP6 as the current electrode pair, and selects the abdominal electrode pair AP5 as the voltage electrode pair. In other words, the terminal switch unit 22 electrically connects the abdominal electrode pair AP6 with the constant current generation unit 21 and electrically connects the abdominal electrode pair AP5 with the potential difference detection unit 23 based on the control of the controller 10 (step S16).

The constant current generation unit 21 flows current between the abdominal electrodes A16 and A26 of the abdominal electrode pair AP6 based on the control of the controller 10 (step S18).

In this state, the potential difference detection unit 23 detects the potential difference between the abdominal electrodes A15 and A25 of the abdominal electrode pair AP5 based on the control of the controller 10 (step S20).

The controller 10 selects the abdominal electrode pairs AP7 and AP8 as the voltage electrode pair in order. That is, the terminal switch unit 22 electrically connects the abdominal electrode pairs AP7 and AP8 with the potential difference detection unit 23 in order based on the control of the controller 10 (step S16). The potential difference detection unit 23 then detects the potential difference between the electrodes of each of the abdominal electrode pairs AP7 and AP8 in order based on the control of the controller 10 (step S20).

Similarly, the controller 10 selects the abdominal electrode pairs AP7 and AP8 as the current electrode pair in order, selects the abdominal electrode pair other than the current electrode pairs of the abdominal electrode pairs AP5 to AP8 in order for each of the abdominal electrode pairs AP7 and AP8, and detects the respective potential difference between the electrodes of the voltage electrode pairs (steps S16 to S20).

When application of current and detection of potential difference are terminated with respect to the combination of all electrode pairs (YES in step S21), the impedance calculating section 12 calculates the impedances Zs1 to Zs24 based on the value of the current flowed by the constant current generation unit 21 and each potential difference detected by the potential difference detection unit 23 (step S22). The values of the impedances Zs1 to Zs24 calculated by the impedance calculating section 12 are temporarily saved in the memory 29, for example.

The visceral fat mass calculation part 16 then calculates the visceral fat area Sv based on the physical information (waist length) accepted by the controller 10 in step S2, the impedances Zt1 to Zt8, and the impedances Zs1 to Zs24 (step S24). The visceral fat area Sv is calculated by equation (1). When the body fat measurement device includes eight abdominal electrode pairs AP1 to AP8, as in the second embodiment of the present invention, an average value of the eight impedances Zt1 to Zt8 is substituted to the impedance Zt of equation (1), and an average value of the twenty-four impedances Zs1 to Zs24 is substituted to the impedance Zs of equation (1).

The subcutaneous fat mass calculation part 17 calculates the subcutaneous fat area Ss based on the physical information (waist length) accepted by the controller 10 in step S2, and the impedances Zs1 to Zs24 (step S26). The subcutaneous fat area Ss is calculated by equation (2). When the body fat measurement device 1 includes four abdominal electrode pairs AP1 to AP8, as in the second embodiment of the present invention, the average value of the twenty-four impedances Zs1 to Zs24, for example, is substituted to the impedance Zs of equation (2).

The body fat mass calculation part 14 calculates the fat free mass FFM based on the subject information (e.g., height) inputted in step S2 and the impedances Zt1 to Zt8 (step S28). The fat free mass FFM is calculated by equation (3). When the body fat measurement device 1 includes eight abdominal electrode pairs AP1 to APB, as in the second embodiment of the present invention, the average value of the eight impedances Zt1 to Zt8, for example, is substituted to the impedance Zt of equation (3).

The body fat mass calculation part 14 calculates the body fat percentage based on the subject information (weight) inputted in step S2 and the fat free mass FFM calculated in step S28 (step S30). The body fat percentage is calculated from equation (4).

The display unit 26 displays each measurement result based on the control of the controller 10 (step S32).

The body fat measurement device 1 then terminates the body fat measurement process.

Note that a typical value of the impedances Zt1 to Zt8 is about 5 Ω. A typical value of the impedances Zs1 to Zs24 is about 80 Ω.

Other configurations and operations are similar to the body fat measurement device according to the first embodiment, and thus detailed description thereof will not be repeated.

Therefore, in the body fat measurement device according to the second embodiment of the present invention, the visceral fat mass is calculated based on the potential difference detected at the back surface of the abdomen of the subject and the potential difference detected at the front surface of the abdomen of the subject, and thus the visceral fat mass can be more accurately measured compared to the body fat measurement device according to the first embodiment of the present invention.

In the body fat measurement device according to the second embodiment of the present invention, the visceral fat mass calculation part 16 calculates the visceral fat mass based on the impedance corresponding to both the front surface of the abdomen and the back surface of the abdomen, but the present invention is not limited thereto. The visceral fat mass calculation part 16 may select the impedance corresponding to either the front surface of the abdomen or the back surface of the abdomen and calculate the visceral fat mass. For example, the visceral fat mass calculation 16 may select the larger one of the impedance corresponding to the front surface of the abdomen or the impedance corresponding to the back surface of the abdomen.

The visceral fat mass calculation part 16 may select the larger one of the visceral fat mass based on the measurement result at the front surface of the abdomen or the visceral fat mass based on the measurement result at the back surface of the abdomen.

The visceral fat mass calculation part 16 may be configured to calculate the representative value of the visceral fat mass based on a predetermined condition such as obtaining the average value of the visceral fat mass based on the measurement result at the front surface of the abdomen and the visceral fat mass based on the measurement result at the back surface of the abdomen and setting the same as the representative value.

The embodiments disclosed herein are illustrative in all aspects and should not be construed as being restrictive. The scope of the invention is defined by the claims rather than by the description given above, and all modifications equivalent in meaning to the claims and within the scope thereof are intended to be encompassed therein.

The invention claimed is:

1. A method of measuring visceral fat mass of a subject, the method comprising:
    arranging a first electrode pair and a second electrode pair on a surface of a back of the subject at a level of an abdomen of the subject, wherein:
        the first and second electrode pairs each include electrodes spaced from each other in a body axis direction, and
        the first and the second electrode pairs are spaced apart from each other in a direction perpendicular to the body axis direction;
    flowing a current between the electrodes of the first electrode pair with a current generation unit;
    detecting a potential difference between the electrodes of the second electrode pair when current is flowed between the electrodes of the first electrode pair with a potential difference detection unit; and
    calculating the visceral fat mass of the subject based on the detected potential difference between the electrodes of the second electrode pair with a visceral fat mass calculation part.

2. The method of claim 1, further comprising arranging the second electrode pair in the body axis direction spaced apart from an axis passing through the electrodes of the first electrode pair on the surface of the back of the subject at the level of the abdomen of the subject.

3. The method of claim 1, further comprising arranging each electrode of the second electrode pair and a corresponding electrode of the first electrode pair in a line in a direction substantially perpendicular to the body axis.

4. The method according to claim 1, wherein the visceral fat mass of the subject is calculated based on the detected potential difference between the electrodes of the second electrode pair and physical information of the subject.

5. The method according to claim 4, wherein the physical information includes an abdominal width and an abdominal thickness of the subject.

6. The method according to claim 1, further comprising:
    calculating an impedance of the subject between the electrodes of the first electrode pair based on the detected potential difference between the electrodes of the second electrode pair with an impedance calculating section, wherein the visceral fat mass of the subject is calculated based on the calculated impedance.

7. A method of measuring visceral fat mass of a subject, the method comprising:

arranging a first electrode pair, a second electrode pair, a third electrode pair, and a fourth electrode pair on a surface of a back of the subject at a level of an abdomen of the subject, wherein:

the first, second, third, and fourth electrode pairs each include electrodes spaced from each other in a body axis direction, and the first, second, third, and fourth electrode pairs are spaced apart from each other in a direction perpendicular to the body axis direction;

selectively flowing a current between the electrodes of the first electrode pair and the electrodes of the third electrode pair with a current generation unit;

detecting a potential difference between the electrodes of the second electrode pair when current is flowed between the electrodes of the first electrode pair, and a potential difference between the electrodes of the fourth electrode pair when current is flowed between the electrodes of the third electrode pair, with a potential difference detection unit; and calculating the visceral fat mass of the subject based on the detected potential difference between the electrodes of the second electrode pair when current is flowed between the electrodes of the first electrode pair, and the detected potential difference between the electrodes of the fourth electrode pair when current is flowed between the electrodes of the third electrode pair, with a visceral fat mass calculation part.

8. A method of measuring visceral fat mass of a subject, the method comprising:

arranging a first electrode pair and second electrode pair on a surface of a back of the subject at a level of an abdomen of the subject, wherein:

the first and second electrode pairs each include electrodes spaced from each other in a body axis direction, and the first and second electrode pairs are spaced apart from each other in a direction perpendicular to the body axis direction;

arranging a third electrode pair at a pair of different sites distant from the abdomen of the subject;

selectively flowing a current between the electrodes of the first electrode pair and the electrodes of the third electrode pair with a current generation unit;

detecting a potential difference between the electrodes of the second electrode pair when current is flowed between the electrodes of the first electrode pair, and a potential difference between the electrodes of the second electrode pair when current is flowed between the electrodes of the third electrode pair, with a potential difference detection unit; and calculating the visceral fat mass of the subject based on the detected potential difference between the electrodes of the second electrode pair when current is flowed between the electrodes of the first electrode pair, and the detected potential difference between the electrodes of the second electrode pair when current is flowed between the electrodes of the third electrode pair, with a visceral fat mass calculation part.

9. The method according to claim 8, wherein the pair of different sites includes a surface of an upper limb of the subject, and a surface of a lower limb of the subject.

10. The method according to claim 9, further comprising:

calculating an impedance Zt based on an amount of the current flowing between the electrodes of the third electrode pair;

calculating an impedence Zs based on the detected potential difference between the electrodes of the second electrode pair; and calculating a visceral fat area Sv according to the following equation (1):

$$Sv = a \times W^2 - b \times (1/Zt) - c \times W \times Zs - d \qquad (1)$$

wherein a, b, and c are coefficients, d is a constant, and W represents a waist length of the subject.

* * * * *